US00PP30572P3

(12) United States Plant Patent
Meilland

(10) Patent No.: US PP30,572 P3
(45) Date of Patent: Jun. 18, 2019

(54) SHRUB ROSE PLANT NAMED 'MEIKAQUINZ'

(50) Latin Name: *Rosa hybrida*
Varietal Denomination: Meikaquinz

(71) Applicant: The Conard-Pyle Company, West Grove, PA (US)

(72) Inventor: Alain Antoine Meilland, Antibes (FR)

(73) Assignee: THE CONARD-PYLE COMPANY, West Grove, PA (US)

( * ) Notice: Subject to any disclaimer, the term of this patent is extended or adjusted under 35 U.S.C. 154(b) by 0 days.

(21) Appl. No.: 15/731,816

(22) Filed: Aug. 8, 2017

(65) Prior Publication Data

US 2019/0053409 P1 Feb. 14, 2019

(51) Int. Cl.
*A01H 5/02* (2018.01)
*A01H 6/74* (2018.01)

(52) U.S. Cl.
USPC ..... Plt./104
CPC ..... *A01H 6/749* (2018.05)

(58) Field of Classification Search
USPC ..... Plt./104
See application file for complete search history.

(56) References Cited

U.S. PATENT DOCUMENTS

PP8,496 P 12/1993 Meilland

*Primary Examiner* — Keith O. Robinson
(74) *Attorney, Agent, or Firm* — Buchanan Ingersoll & Rooney PC

(57) ABSTRACT

A new and distinct variety of shrub rose plant, herein referred to by its cultivar name, 'Meikaquinz', is provided which forms in abundance on a substantially continuous basis attractive, cup-shaped, yellow colored blossoms which emit a strong fragrance. Attractive, semi-glossy, medium green foliage is formed. The disease tolerance is very good, particularly with respect to black spot. The new variety is well suited for proving attractive ornamentation in the landscape.

1 Drawing Sheet

Figures 1, 2, 3, 4, 5, 6, 7, 8, 9, 10, 11, 12, 13, 14, 15:
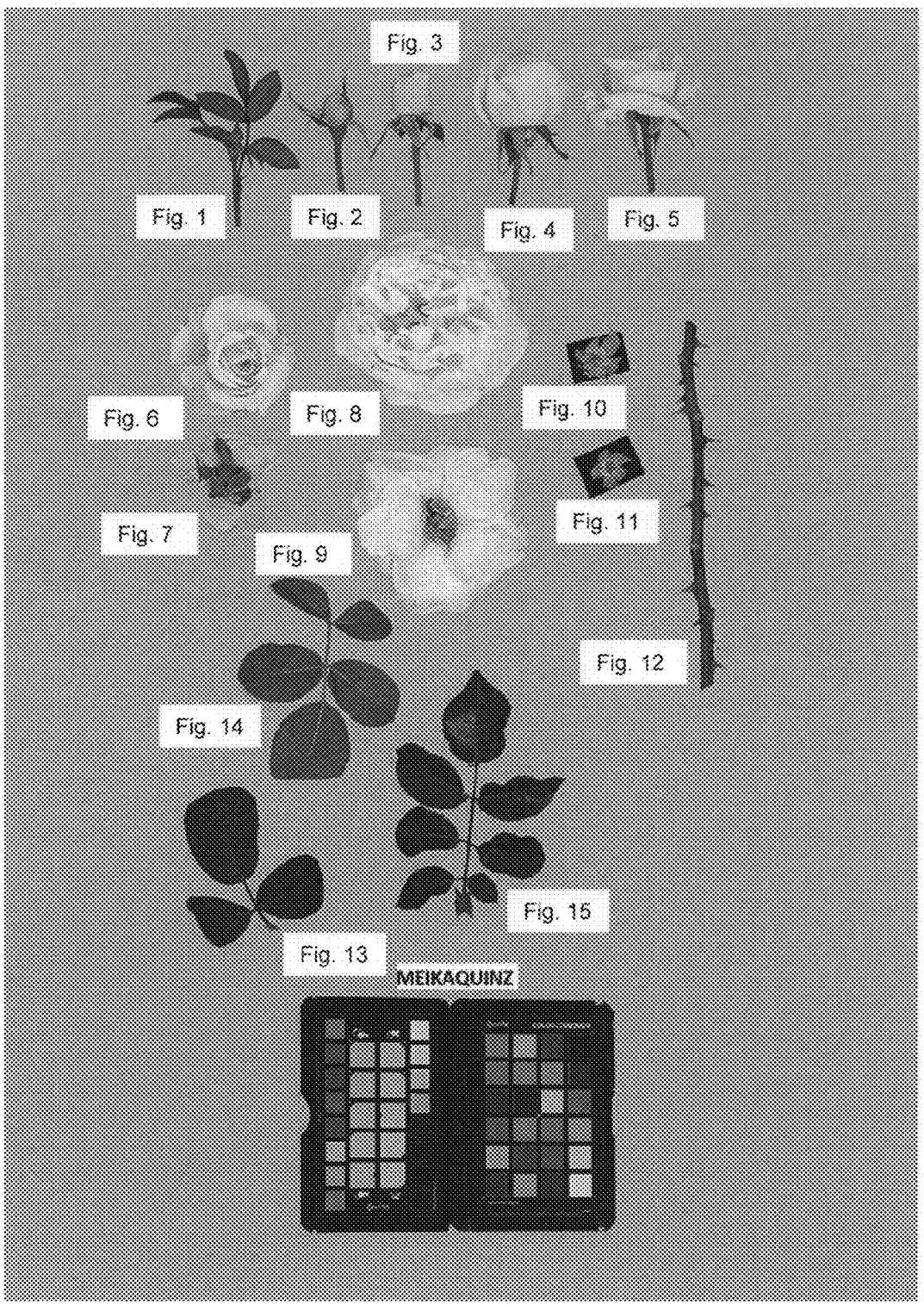

Botanical/commercial classification:
Latin name: *Rosa hybrida.*
Common name: Shrub Rose Plant.
Varietal denomination: 'Meikaquinz'.

SUMMARY OF THE INVENTION

The new variety of *Rosa hybrida* Shrub rose plant was created by artificial pollination wherein two parents were crossed which previously had been studied in the hope that they would contribute the desired characteristics. The female parent (i.e., the seed parent) was an unnamed seedling (non-patented) which was the product of the cross of the 'MEIRONSSE' variety (U.S. Plant Pat. No. 8,496) and 'MEIPSILON' variety (non-patented). The male parent (i.e., the pollen parent) was the 'AUSMAS' variety (non-patented in the United States).

The parentage of the new variety can be summarized as follows:

('MEIRONSSE'×'MEIPSILON')×'AUSMAS'

The seeds resulting from the above pollination were sown and small plants were obtained which were physically and biologically different from each other. Selective study resulted in the identification of a single plant of the new variety.

It was found that the new variety of Shrub rose plant of the present invention:

(a) abundantly and substantially continuously forms attractive, cup-shaped, yellow blossoms which emit a strong fragrance, (b) forms attractive, ornamental, semi-glossy foliage,
(c) exhibits excellent resistance to pests and diseases, particularly with respect to black spot, and
(d) is well suited for providing attractive ornamentation.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'Meironsse' variety displays darker salmon colored blossoms and the 'Meipsilon' variety displays bicolor red and yellow blossoms, while the new variety displays yellow blossoms. The 'Ausmas' variety exhibits 35 petals on average while the new variety displays 50 petals on average under normal conditions. Moreover, the new variety can be readily distinguished from other similar non-parental varieties. For example, the 'Meilivar' variety exhibits a turbinate bud, whereas the new variety exhibits a rounded bud and is more compact than the 'Meilivar' variety.

The new variety has been found to undergo asexual propagation in France by a number of routes, including budding, grafting, and the use of cuttings, such as node cuttings, node stem with a leaf. Asexual propagation by the above-mentioned techniques in France has shown that the characteristics of the new variety are stable and are strictly transmissible by such asexual propagation from one generation to another. Accordingly, the new variety undergoes asexual propagation in a true-to-type manner.

The new variety has been named 'Meikaquinz'.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were approximately two years of age and were observed during September while budded on own roots and growing outdoors at Le Cannet des Maures, Var, France. Standard color information is included at the bottom of the photograph.

FIG. 1—illustrates a specimen of a young shoot.

FIG. 2—illustrates a specimen of a floral bud before the opening of the sepals.

FIG. 3—illustrates a specimen of a floral bud at the opening of the sepals.

FIG. 4—illustrates a specimen of a floral bud at the opening to the petals.

FIG. 5—illustrates a specimen of a flower in the course of opening.

FIG. 6—illustrates a specimen of a flower in the course of opening—plan view—obverse.

FIG. 7—illustrates a specimen of a flower in the course of opening—plan view—reverse.

FIG. 8—illustrates a specimen of a fully open flower—plan view—obverse.

FIG. 9—illustrates a specimen of a fully open flower—plan view—reverse.

FIG. 10—illustrates a specimen of a floral receptacle showing arrangement of the stamens and pistils.

FIG. 11—illustrates a specimen of a floral receptacle showing arrangement of the pistils (stamens removed).

FIG. 12—illustrates a specimen of a flowering stem.

FIG. 13—illustrates a specimen of a leaf with 3 leaflets—plan view—upper surface.

FIG. 14—illustrates a specimen of a leaf with 5 leaflets—plan view—under surface.

FIG. 15—illustrates a specimen of a leaf with 7 leaflets—plan view—upper surface.

DETAILED BOTANICAL DESCRIPTION

The chart used in the identification of the colors is that of The Royal Horticultural Society (R.H.S. Colour Chart, 2001 edition), London, England. The terminology which precedes reference to the chart has been added to indicate the corresponding color in more common terms. The description is based on the observation of two-year-old specimens of the new variety during September while budded on their own roots and growing outdoors at Le Cannet des Maures, Var, France.

Class: Shrub Rose Plant.

Plant:

*Habit.*—Shrub.

Branches:

*Color.*—Young stems: commonly near Green Group 137C. Adult wood: commonly near Green Group 137C.

*Thorns.*—Configuration on adult stems: curved downward on the upper surface and concave on the under surface. Size: commonly approximately 8 mm in length on average. Base shape: oval. Quantity: commonly approximately 5 thorns per 10 cm long young stem and commonly approximately 4 thorns per 10 cm long adult stem. Color: commonly near Greyed Purple Group 185C on young stems and commonly near Greyed Orange Group 175B on adult stems. Small prickles <0.7 cm: commonly absent.

Foliage:

*General appearance.*—Very dense with semi-glossy aspect.

*Number of leaflets.*—3, 5, and 7; most often 5 or 7.

*Terminal leaflet.*—Length: approximately 6.2 cm on average. Width: approximately 4.8 cm on average.

*New foliage.*—Upper surface color: commonly near Yellow Green Group 146B. Under surface color: commonly near Yellow Green Group 146C.

*Adult foliage.*—Upper surface color: commonly near Green Group 137C. Under surface color: commonly near Green Group 138C.

Leaflets:

*Shape.*—Tip: cuspidate. Base: rounded.

*Texture.*—Leathery.

*General appearance.*—Elliptical.

*Edge.*—Slightly denticulate.

*Serration.*—Small and single.

*Petiole rachis.*—Color of upper surface: commonly near Yellow Green Group 144C. Color of under surface: commonly near Green Group 138C.

*Petioles.*—Upper surface: no glandular. Under surface: 1 to 2 prickles on average. Color of upper surface: commonly near Green Group 137C. Color of under surface: commonly near Green Group 138C. Petiole length of terminal leaflet: near 3.5 cm on average.

*Stipules.*—General appearance: adnate, pectinate and rather broad. Length: approximately 2 cm on average. Width: near 0.7 cm on average. Color of upper surface: commonly near Yellow Green Group 144C. Color of under surface: commonly near Green Group 138D.

Inflorescence:

*Number of flowers per stem.*—Generally between 1 and 3 flowers per stem.

*Bud.*—Shape: conical. Length: approximately 2.5 cm on average. Width: approximately 2.4 cm on average. Color as calyx breaks: upper surface: commonly near Yellow Group 8C. under surface: commonly near Yellow Group 8C.

*Sepals.*—Length: approximately 2.2 cm on average. Width: approximately 0.9 cm on average. Shape: no extension, at the top: none elongated, at the base: upright. Upper surface: texture: smooth. color: commonly near Yellow Green Group 146D. Under surface: texture: tomentous. color: commonly near Green Group 137C.

*Receptacle.*—Color: commonly near Yellow Green Group 146D. Length: approximately 0.6 cm on average. Width: approximately 0.6 cm on average. Surface: smooth. Shape: funnel shaped.

*Peduncle.*—Length: approximately 5-6 cm on average. Width: approximately 0.6 cm on average. Surface: smooth. Color: commonly near Green Group 137C.

*Flower.*—Average diameter when fully open: approximately 12 cm on average. Shape: cup shaped. Type: very double. Profile of the lower part of the flower: concave. Number of petals under normal conditions: approximately 50 petals on average. Shape of the petal: base: obtuse. top: rounded. Texture of the petal: leathery. Petal length: approximately 4.2 cm on average. Petal width: approximately 4 cm on average. Petal arrangement: imbricated without petaloids. Petal drop: petals drop off cleanly before drying. Fragrance: strong, main fragrances of the perfume are tea, apple, cucumber, and alfalfa. Basal spot: present on the inner side of the petal; approximately 5 mm on average, and commonly near Yellow Group 9A. Color when opening: upper surface: commonly near Yellow Group 8B. under surface: commonly near Yellow Group 8B. Color of the open flower: upper surface: commonly near Yellow Group 8C. under surface: commonly near Yellow Group 8C. Anthers: number is approximately 92 on average, length is approximately 0.2 cm on average, coloration is commonly near Orange Red Group 34C, and arrangement is regular around styles. Filaments: length is approximately 0.4 cm on average and coloration is commonly near Yellow Group 2D. Styles: length is approximately 0.1 cm on average, the coloration is commonly near Yellow Group 2D, and the number is approximately 63 on average. Stigmas: size is approximately 0.5 cm on average and the coloration is commonly near Red Group 44C.

Development:

*Vegetation.*—Strong.

*Blooming.*—Early in the season, normal and nearly continuous.

*Tolerance to disease.*—Very good, and particularly against *Diplocarpon rosae* black spot.

The new 'Meikaquinz' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of shrub rose plant characterized by the following combination of characteristics:

(a) abundantly and substantially continuously forms attractive, cup-shaped, yellow blossoms which emit a strong fragrance, (b) forms attractive, ornamental, semi-glossy foliage, (c) exhibits excellent resistance to pests and diseases, particularly with respect to black spot, and (d) is well suited for providing attractive ornamentation; substantially as herein shown and described.

* * * * *

MEIKAQUINZ